US009813985B2

(12) United States Patent
Shapley et al.

(10) Patent No.: US 9,813,985 B2
(45) Date of Patent: Nov. 7, 2017

(54) HANDSET DEVICE

(71) Applicant: Cellnovo Limited, Swansea (GB)

(72) Inventors: Julian Shapley, Swansea (GB); Matthew Powell, Swansea (GB); Anthony Martin, Swansea (GB)

(73) Assignee: Cellnovo Limited, Swansea (GB)

( * ) Notice: Subject to any disclaimer, the term of this patent is extended or adjusted under 35 U.S.C. 154(b) by 0 days.

(21) Appl. No.: 15/114,837

(22) PCT Filed: Jan. 30, 2015

(86) PCT No.: PCT/GB2015/050249
§ 371 (c)(1),
(2) Date: Jul. 27, 2016

(87) PCT Pub. No.: WO2015/114371
PCT Pub. Date: Aug. 6, 2015

(65) Prior Publication Data
US 2016/0353375 A1 Dec. 1, 2016

(30) Foreign Application Priority Data

Jan. 30, 2014 (GB) .................................. 1401590.3

(51) Int. Cl.
*H04W 52/02* (2009.01)
*G06F 19/00* (2011.01)
*H04W 4/00* (2009.01)

(52) U.S. Cl.
CPC .... *H04W 52/0209* (2013.01); *G06F 19/3418* (2013.01); *G06F 19/3468* (2013.01);
(Continued)

(58) Field of Classification Search
CPC ......... H04W 52/0209; H04W 52/0206; H04W 4/008; G06F 19/3418; G06F 19/3468
See application file for complete search history.

(56) References Cited

U.S. PATENT DOCUMENTS

2004/0122489 A1 6/2004 Mazar et al.
2006/0292987 A1 12/2006 Ophir et al.
(Continued)

FOREIGN PATENT DOCUMENTS

GB 2443261 4/2008

OTHER PUBLICATIONS

ISA/EPO, "International Search Report and Written Opinion", for PCT application No. PCT/GB2015/050249, dated Jul. 1, 2015, 18 pages.

*Primary Examiner* — Leon Flores
(74) *Attorney, Agent, or Firm* — Kang S. Lim

(57) ABSTRACT

A handset device is described, which comprises a first radio transceiver for receiving status information from a medical device worn by a patient, the first radio transceiver being operable only while the handset device is in an active state, and a second radio transceiver for communicating the status information to a remote server, the second radio transceiver being inoperable when the handset device is in the active state. The handset device also comprises a controller, responsive to a first predetermined condition to transition the handset device from the active state to a low power state in which both the first radio transceiver and the second radio transceiver are inoperable. During the transition from the active state to the low power state, the second radio transceiver is used to communicate the status information to the remote server. This process enables status data to be synchronized periodically to the remote server without impairing the function of the medical device. More particularly, this process advantageously triggers synchronization such that (a) the user does not have to take any action to cause synchronization, (b) the synchronization occurs at a time when it is safe for an RF transmission to the server to occur, (Continued)

and (c) the synchronization is timely—that is, updates are sent soon after they have been logged on the handset device.

18 Claims, 2 Drawing Sheets

(52) U.S. Cl.
CPC ....... *H04W 4/008* (2013.01); *H04W 52/0206* (2013.01); *Y02B 60/50* (2013.01)

(56) References Cited

U.S. PATENT DOCUMENTS

| | | |
|---|---|---|
| 2007/0281617 A1 | 12/2007 | Meylan et al. |
| 2009/0076359 A1 | 3/2009 | Peyser |
| 2010/0137784 A1 | 6/2010 | Cefai et al. |
| 2011/0093286 A1* | 4/2011 | Dicks .................. A61B 5/0022 705/2 |
| 2011/0316562 A1 | 12/2011 | Cefai et al. |
| 2012/0182939 A1 | 7/2012 | Rajan et al. |
| 2012/0266251 A1 | 10/2012 | Birtwhistle et al. |
| 2015/0057634 A1* | 2/2015 | Mastrototaro ...... A61M 5/1723 604/500 |
| 2015/0057807 A1* | 2/2015 | Mastrototaro ......... G05B 15/02 700/275 |

* cited by examiner

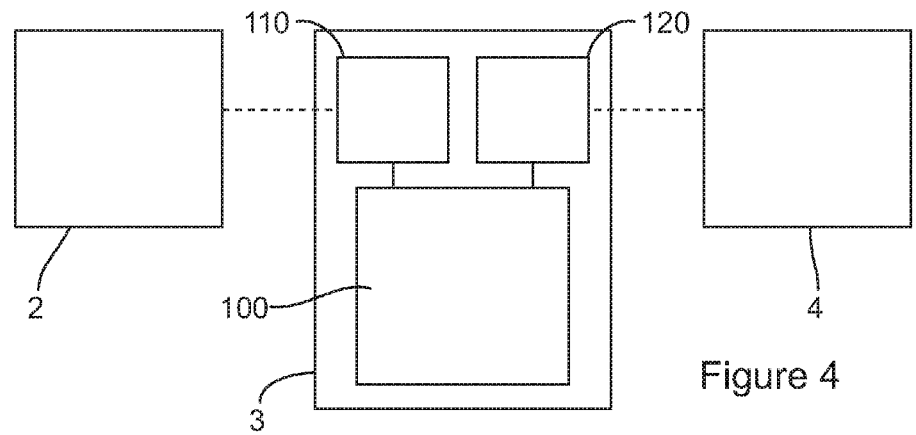
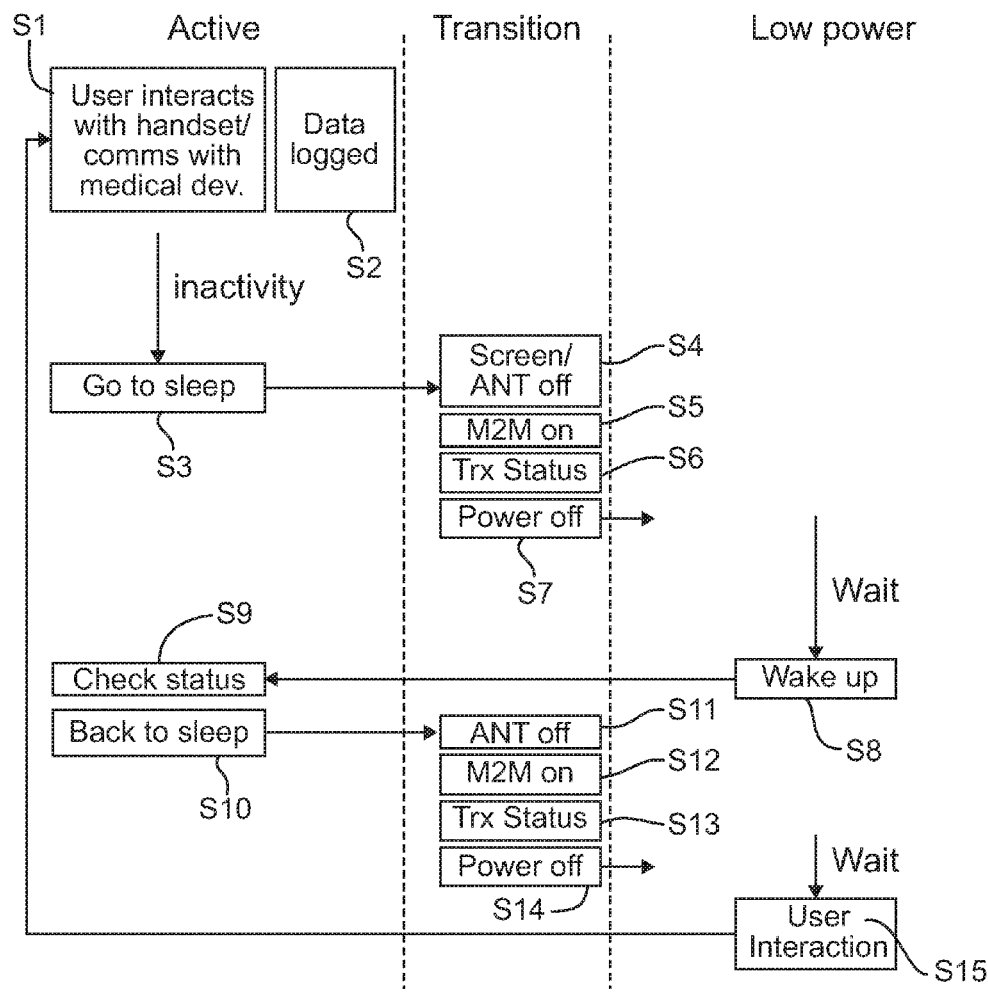

HANDSET DEVICE

CROSS-REFERENCE TO RELATED APPLICATIONS

The present application is a United States National Stage entry under 35 U.S.C. §371 of International Application No. PCT/GB2015/050249 filed Jan. 30, 2015, designating the United States of America and published in English on Aug. 6, 2015, which in turn claims priority to Great Britain Application No. 1401590.3, filed Jan. 30, 2014, each of which is incorporated herein by reference in their entirety.

FIELD OF THE INVENTION

The present invention relates to a handset device for communicating with a medical device worn by a patient and a remote server.

BACKGROUND TO THE INVENTION

Conventionally, Type 1 diabetes has been treated with daily insulin injections. However, this inevitably results in insulin levels that do not match the normal and rapid changes in blood glucose which occur in a patient throughout the day. On the one hand, insufficient insulin and high glucose levels lead to immediate symptoms and contribute to long-term complications. On the other hand, too much insulin may result in too little blood sugar leading to loss of consciousness and convulsions. As an alternative to injections, insulin pump therapy is intended to mimic the normal physiology of the healthy pancreas. Unlike multiple daily insulin injections, an insulin pump is able to provide a constant background infusion of insulin that can be adjusted according to individual need, compensating for daily activity and exercise routines. The pump may also be programmed to deliver bolus doses of insulin to address the big glucose swings in the blood that would otherwise result from eating and drinking. By mimicking the natural physiology of the pancreas, insulin pump therapy aims to maintain a constantly normal blood glucose level; avoiding the highs that are associated with meals or the lows that come from too much insulin.

In a system in which the pump is wirelessly controlled by a handset device, and in which the handset device is required to receive status information from the pump and transmit it to a remove server, it has been recognised that there is a problem that the wireless transmission from the handset device to the server may interfere with control commands being sent to the pump, potentially causing an incorrect dosage of insulin to be administered by the pump. Embodiments of the present invention seek to address this problem.

SUMMARY OF THE INVENTION

According to an aspect of the present invention, there is provided a handset device, comprising:

a first radio transceiver for receiving status information from a medical device worn by a patient, the first radio transceiver being operable only while the handset device is in an active state;

a second radio transceiver for communicating the status information to a remote server, the second radio transceiver being inoperable when the handset device is in the active state; and a controller, responsive to a first predetermined condition to transition the handset device from the active state to a low power state in which both the first radio transceiver and the second radio transceiver are inoperable;

wherein, during the transition from the active state to the low power state, the second radio transceiver is used to communicate the status information to the remote server.

This process enables status data to be synchronised periodically to the remote server without impairing the function of the medical device. More particularly, this process advantageously triggers synchronisation such that (a) the user does not have to take any action to cause synchronisation, (b) the synchronisation occurs at a time when it is safe for an RF transmission to the server to occur, and (c) the synchronisation is timely—that is, updates are sent soon after they have been logged on the handset device.

The present invention recognises that it may not be necessary to provide for constant communication with the medical device. Even in the case of an insulin pump or other therapeutic product delivery device, such a device can operate independently of the handset once a basal dose has been set by the handset. Similarly, it is not necessary to provide for constant communication with the remote server. Information can be buffered at the handset until an appropriate opportunity arises to initiate a communication with the remote server. Moreover, it is desirable that, to increase battery life on the handset (between recharges), the handset switch into a low power state for periods of time during which it is not required. It has been recognised that the communication of status information to the server can be conducted as part of the transition from the active state to the low power state of the handset. It will be appreciated that, at this time there will be no risk of the transmission to the server interfering with control commands being transmitted to the medical device, since the transition from the active state to the low power state only occurs when the handset is not required to communicate with the medical device.

The status information may comprise information about the medical condition of the user, and/or information about the state of the medical device.

During the transition from the active state to the low power state, a display screen of the handset device may be switched off, and remain off while the handset device is in the low power state. The first predetermined condition (under which the handset transitions to the low power state) may be a user input to the handset device, such as selecting a "sleep" function on a user interface to the handset device. The first predetermined condition may also be the non-use of the handset device for a predetermined period of time; that is, the handset device may power down into the low power state after a period of inactivity.

The first radio transceiver may be one of a Bluetooth transceiver or an ANT transceiver. The second radio transceiver may be one of a WiFi transceiver, a mobile telecommunications network transceiver or a GSM radio transceiver. Generally speaking, the first radio transceiver may be of a lower power level than the second radio transceiver, with possible effect that a transmission using the second radio transceiver may drown out or corrupt a transmission using the first radio transceiver, potentially causing a reception error at the medical device.

The medical device may be a therapeutic product delivery device, in which case the handset device may control the operation of the therapeutic product delivery device. The therapeutic product delivery device may be an insulin pump. In this case, the first radio transceiver may be used to carry control signals from the handset device to the therapeutic product delivery device to control the amount and/or timing of the delivery of a therapeutic product to the patient.

Alternatively, the medical device may be a glucose meter. Further, the first radio transceiver may be operable to receive status information from a plurality of medical devices, for example from both an insulin pump and a glucose meter.

The controller may be responsive to a second predetermined condition to transition the handset device from the low power state to the active state. The second predetermined condition may be a user input to the handset. The second predetermined condition may also be the handset having been in the low power state for a predetermined time period; that is, the handset may wake itself up periodically to check the status of the medical device, and then transition back to the low power state again (thereby automatically triggering the relaying of the newly acquired status information to the remote server). More specifically the controller may be responsive to the handset having been in the low power state for a predetermined time period to transition the handset device from the low power state to the active state, obtain status information from the medical device via the first radio transceiver, and initiate a return transition from the active state to the low power state, wherein during the return transition from the active state to the low power state, the second radio transceiver is used to communicate the status information obtained from the medical device to the remote server.

According to another aspect of the present invention, there is provided a method of synchronising data between a handset device and a remote server, the handset having a first radio transceiver for receiving status information from a medical device worn by a patient, the first radio transceiver being operable only while the handset device is in an active state, and a second radio transceiver for communicating the status information to a remote server, the second radio transceiver being inoperable when the handset device is in the active state, the method comprising the steps of:

responsive to a first predetermined condition, transitioning the handset device from the active state to a low power state in which both the first radio transceiver and the second radio transceiver are inactive; and during the transition from the active state to the low power state, communicating the status information to the remote server using the second radio transceiver.

Various other aspects and features of the present invention are described in the embodiments which follow.

DETAILED DESCRIPTION

The invention will now be described by way of example with reference to the following Figures in which:

FIG. 4 shows a schematic view of the handset, drug delivery device and server; and FIG. 5 schematically illustrates how the handset transitions between active and low power states.

SYSTEM

Figure 1:
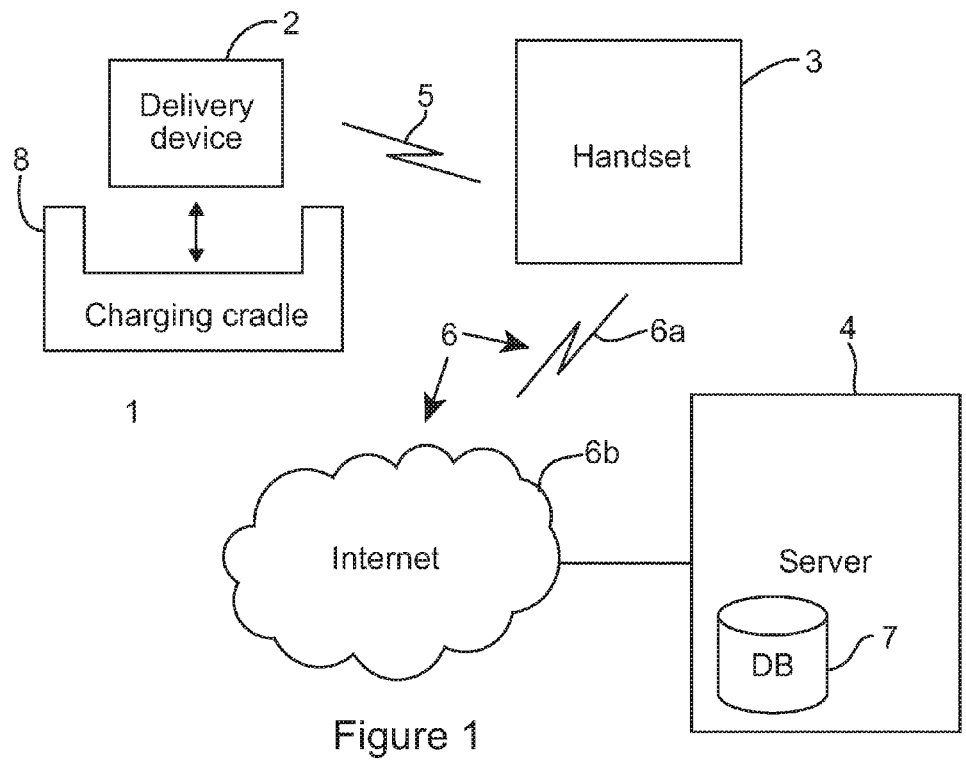
FIG. 1 shows a schematic view of a drug delivery system.

Referring to FIG. 1, a drug delivery system 1 is schematically illustrated. The drug delivery system 1 in this case delivers insulin to a patient. However, it will be appreciated that embodiments of the present invention may be appropriate for delivering drugs other than insulin. The system 1 comprises a delivery device 2 which is worn on the patient's body, a handset 3 (which may appear similar to a smartphone) for controlling the delivery device 2, and a server 4. The delivery device 2 and the handset 3 are able to communicate via a first wireless connection 5, for example a lower power ANT radio connection. The handset 3 and the server 4 are able to communicate via a second wireless connection 6, for example a GPRS mobile data connection 6a and the Internet 6b. The server 4 comprises a patient database 7 for storing patient medical information and other information about the patient. Both the delivery device 2 and the handset 3 are powered by rechargeable batteries. Also shown in FIG. 1 is a charging cradle 8 into which the delivery device 2 is inserted in order to charge the delivery device 2.

Delivery Device

Figure 2:
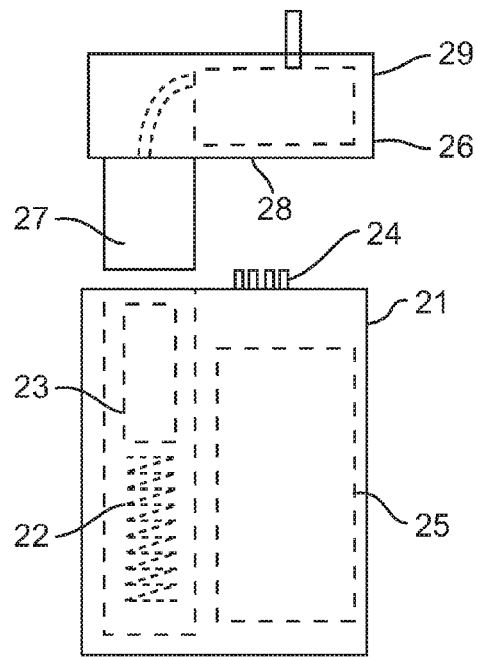
FIG. 2 shows a schematic view of a drug delivery device.
Figure 3:
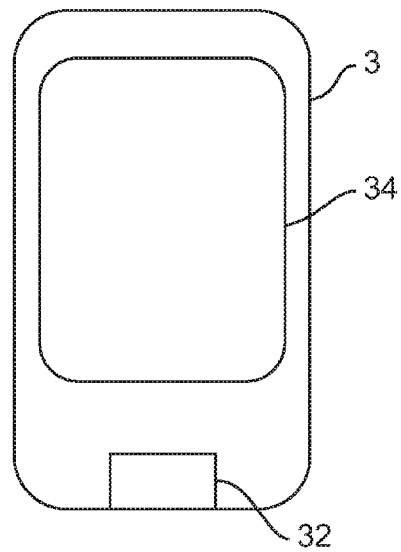
FIG. 3 shows a schematic view of a handset for controlling the drug delivery device of FIG. 2.

The delivery device comprises two parts, which are detachable from each other, as shown schematically in FIG. 2. The first of the two parts is a body 21, which contains a spring 22, a biasing member 23 including a displacement sensor (for example as described in US2011/0316562), and a set of contact pins 24 for providing an electrical connection with the second part. The body 21 also comprises a battery, control circuitry and a transceiver for communicating with the handset, which are not separately shown in FIG. 2 in the interests of clarity, but are generally represented by element 25. The second of the two parts is a disposable insulin cartridge 26, which comprises a reservoir 27 of insulin, contact pads 28 for providing an electrical connection with the body 21 via the pins 24, a pumping device (a wax actuator, for example as described in GB2443261) for pumping the insulin from the reservoir 27 into the patient's body, and a valve arrangement (for example as described in US2010/0137784). The pumping device and valve arrangement are not separately shown in FIG. 2 in the interests of clarity, but are generally represented by element 29. It will be understood that the body 21 of the delivery device is reusable, while the disposable cartridge 26 is intended to be removed and disposed of when the reservoir 27 has been depleted, or when the cartridge has passed its use by date, or if it develops a fault. A new cartridge can then be engaged with the body 21. While it is preferable that the cartridge is disposable, it will be appreciated that, in principle, the cartridge may be refilled and reused again rather than being disposed of. However, even in this case the cartridge should be removable from the body so that a new (full) cartridge can be used while the original cartridge is being refilled.

In use, the body 21 and the cartridge 26 of the delivery device 2 are physically and electrically connected. The electrical connection is via the pins 24 and pads 28. The physical connection may be provided by clips or any other releasable engagement mechanism (not shown). The control circuitry in the body 21 is responsive to control signals received from the handset 3 via the wireless connection 5 to draw current from the battery and apply an electrical current via the pins 24 and the pads 28 to activate the pumping device within the cartridge 26 to draw fluid from the reservoir 27 through the valve arrangement and out of the delivery device 2 to a patient's body. The rate of delivery of the therapeutic product can be controlled by the control circuitry to achieve a particular basal delivery rate, or bolus dose, by controlling the amount and timing of electrical current to the pumping device. Although the basal rate is set by the handset, once set the delivery device 2 is able to maintain the set basal rate with no further communication from the handset 3. As can be seen in FIG. 2, when the body 21 and the cartridge 26 are in engagement, the reservoir 27 is received within the body 21, displacing the biasing member (and displacement sensor) 23 and compressing the spring 22. The compressed spring applies a biasing force to a base of the reservoir 27 via the biasing member 23. The biasing force does not in isolation force insulin from the reservoir 27 through the valve arrangement and into the patient's body, but when combined with the pumping action of the pumping device, the biasing force pressurises the insulin in the reservoir 27 to refill a pumping chamber in advance of each pumping action. It is the pumping action which drives a controlled amount of insulin from the pumping chamber through an outlet valve and to the patient's body. The reservoir takes the form of a cylinder having a first end from which insulin is drawn under the action of the pump, and a second end opposite to the first end at which the (moveable) base is provided. The base of the reservoir moves inwardly of the reservoir (to effectively decrease the size of the reservoir) as the insulin is pumped from the reservoir, under the biasing force provided by the biasing member 23. The position of the biasing member 23 is dependent on the current fill state of the reservoir—that is, how much insulin is remaining in the reservoir. The position of the biasing member 23, and thus the base of the reservoir 27, is determined by the displacement sensor. The displacement sensor is therefore able to generate a signal indicative of the remaining quantity of insulin in the reservoir. By monitoring the change in the remaining quantity of insulin with respect to time, an actual rate of insulin delivery can be determined. This can be used by the control circuitry to apply corrections to the actual delivery rate by adapting the amount and/or timing of electrical current to the pumping device. The quantity of insulin remaining in the reservoir is transmitted to the handset 3, where it can be displayed to the patient and used as an indicator of when the patient should change the current cartridge for a new cartridge. The control circuitry in the body 21 may also transmit an indication of current battery level to the handset, so that the patient is made aware of when the battery requires recharging.

The delivery device also contains an activity monitor to track exercise (not shown). Exercise can have a significant effect on the amount of insulin needed for good control, so tracking exercise accurately is an important part of effective diabetes management. The activity monitor uses a sensor in the delivery device to detect movement of the delivery device, which can be used to infer when the user is engaged in physical activity. The detected activity is then wirelessly communicated to the handset via the wireless connection 5, where the handset (and the server) is able to track and record the patient's activity. Through an online portal to the server, the patient and permitted medical professionals are able to compare activity peaks with blood glucose to identify how activity is influencing the patient's need for insulin. This can in turn be used to program the handset with appropriate dosages for the patient.

Due to the fact that the patient interfaces with the handset rather than the delivery device itself, the delivery device is able to be made small and discreet, and is provided without buttons or a physical connection to a control unit.

Handset

The handset 3 comprises two transceivers. The first transceiver is for communicating with the delivery device via the first wireless connection 5, while the second transceiver is for communicating with the server 4 via the second wireless connection 6. The handset also comprises a processor for running control software. The control software monitors the patient's condition and reports it to the central server 4, and controls the delivery of insulin doses to the patient by transmitting control signals to the delivery device 2. The handset 3 also comprises a touch screen display 34, which displays information to the user and provides a user interface for the user to input data, modify the basal rate, and trigger extraordinary bolas doses.

As well as wirelessly controlling the pump, the handset 3 also has an integral blood glucose meter 32. The blood glucose meter 32 detects the amount of glucose in the patient's blood. The blood may be analysed at the meter 32 by pricking the patient's finger and depositing a droplet of blood on a slide, which is inserted into the meter 32. The detected blood glucose level can be brought to the attention of the patient on the handset 3, and the patient can decide to trigger a bolas dose based on the blood glucose information. The result of every blood glucose test is automatically logged by the software and becomes immediately available for reference via the server 4 to the patient, medical professionals and even family members (such as parents). More generally, the handset 3 runs various software applications which help the user (and other authorised parties) to keep track of diet, insulin, blood glucose and exercise (which as explained above is recorded automatically from a sensor in the delivery device). By automating data collection, the handset 3 eliminates, or at least reduces, the need for a diabetes journal and ensures that comprehensive and accurate clinical information are constantly available to the patient and medical professionals via the server 4.

When controlling the delivery device, the handset 3 sends wireless signals to the delivery device 2 to deliver regular periodic doses of insulin at a pre-determined basal rate, which is set on the handset 3 according to the recommendations of a medical professional. The basal rate may be adjustable by the user within certain constraints. However, the software is configured such that it is not allowed for the basal rate to be adjusted remotely by third parties such as doctors. The hand-held device 3 also allows the user to trigger extraordinary bolus doses, for example after eating carbohydrates or performing exercise. As with a basal dose, the bolus dose is delivered by the delivery device 2 in response to control signals sent wirelessly from the handset 3. The user is able to input the volume of carbohydrates which have been consumed at a relevant time and is also able to input periods of exercise and the hand-held device is able to recommend adjustments to the basal rate or when a bolus is needed. As discussed above, the glucose monitor 32 may have an influence on the dosage. All of this information is transmitted to the server 4. The hand-held device 3 also receives information from the delivery device 2, for example to indicate whether it is faulty or when the insulin cartridge needs to be replaced. It also provides an indication of battery level.

Server

It will be understood from the above that the handset 3 and the delivery device 2 monitor and record clinical information while delivering insulin according to the body's needs. By providing this information to the server 4, it can be made almost immediately available to all those who need to see it. In particular, a mobile connection to a secure online management portal makes it possible for patients, clinicians and parents to be made constantly aware of, and able to react to, changing conditions. A diabetes clinic with patients using the system is able to see the current status of all its patients on a single screen, delivered to the clinic in real time. The portal can be accessed over the Internet in the clinic or through a smartphone. In addition to making it possible for a patient to access their latest clinical information online, it is possible for the patient to see simple visual analysis of their data, for example to identify trends and patterns in their blood sugar, and to immediately see their insulin dosing habits. This information can all be viewed using a simple online web portal that can be accessed from home, from work or from a smartphone. The server can also transmit SMS messages to a child's parents to let them know their child's information and state of health.

A patient using the system is provided with a personal login to the secure mobile diabetes management portal. Once logged in the patient can see all of their automatically collected data in the form of charts and graphs to help them understand where they might need to make adjustments. Exercise habits are mapped out in pie charts. An indication of exactly how and when the patient's insulin was delivered is provided. The patient's clinicians are able to see the same analysis and information, enabling them to call or text the patient whenever needed with guidance and advice.

From a single online dashboard screen, the clinic has access to the status of all the patients on the system; including current blood sugar, average blood sugar, insulin dosing, hypo frequency and blood testing habits. At a glance, anyone having difficulties can easily be identified for an immediate response. With a single click, all the data for a patient is analysed and charted to identify trends, patterns and problems. Using the portal, clinics can completely reorganise the way in which patients are managed. Text and email can be used to check on recent events. Clinic visits are focused completely on current and accurate information.
Synchronisation of the Handset Device with the Server As described above, the handset wirelessly controls the pump to deliver insulin at regular intervals, using a low power transmitter such as an ANT radio transceiver or Bluetooth. The handset also uses a GPRS machine to machine (M2M) data connection to communicate with the remote server, to provide the remote server with status information, some of which relates to the patient's medical condition. Such a data connection, which may be carried over WiFi or 3G for example, uses much higher power radio signals, which may disadvantageously result in the higher powered data connection to the server interfering with the (communications link between the) handset and pump to the extent that an incorrect insulin dose may be given. To address this problem, data is only transmitted to the remote server when the handset is shut down or has gone into hibernation, so as to avoid the risk of any RF interference. In other words, the M2M data connection is not active at all times. Instead, the data (some of which may come from the therapeutic product delivery device, some of which may be local to the handset device (for example blood glucose readings), is logged by the handset device, which periodically transmits the logged data to the remote server/database. This process is referred to as synchronisation.

Referring to FIG. 4, the handset 3 (of FIG. 1) is shown to comprise a controller 100 (a processor), a first radio transceiver 110 for communicating via a low power ANT radio connection with the delivery device 2 and a second radio transceiver 120 for communicating via a high power GPRS M2M connection with the server 4. The first radio transceiver 110 provides for bidirectional communication between the delivery device 2 and the handset 3. The bidirectional communication may comprise status information (e.g. battery fill level of the delivery device, insulin reservoir fill level of the delivery device, any detected faults, information from the activity monitor integrated into the delivery device, and information regarding the amount of insulin delivered) communicated from the delivery device 2 to the handset 3. The bidirectional communication may also comprise control commands (e.g. a basal delivery rate or an instruction to administer a bolus dose) communicated from the handset 3 to the delivery device 2. The first radio transceiver 110 is operable only while the handset device is in an active state (not in a low power state or a transition state, as will be explained below). The second radio transceiver 120 provides for the communication of status information to a remote server. This includes the status information received (and logged) at the handset 3 from the delivery device 2, and also status information originating at the handset itself (e.g. blood glucose readings from the integrated glucose meter, or any information (e.g. consumed calories) entered by the user into the handset device 3. The second radio transceiver is inoperable when the handset device is in the active state, so as not to interfere with the first radio transceiver 110. It will be appreciated that the second radio transceiver 120 (M2M communication link) will not be used when the handset 3 is in the active state (to avoid interference), nor in the low power state (because the device is powered down). The M2M communication link is used only during the transition phase between the active state and the low power state, as will be explained below with reference to FIG. 5.

In FIG. 5, the handset 3 is starting out in an active state. At a step S1, the user of the handset 3 is interacting with the handset (for example entering information, utilising the glucose meter, or initiating a bolus dose), and/or the handset 3 is communicating wirelessly with the delivery device 2 via the low power radio transceiver 110. During this time, at a step S2, data is logged at the handset. The logged data includes status data provided by the delivery device 2, and status data inputted to or generated at the handset 3. Following a period of inactivity, the handset 3 determines that it should go to sleep (switch into a low power mode) at a step S3. The process then enters a transition state, where the screen and the first radio (ANT) transceiver 110 of the handset 3 are switched off at a step S4, the second radio transceiver 120 (M2M link) is switched on at a step S5, the status information is transmitted to the server 4 using the second radio transceiver 120 at a step S6, and then the handset fully powers off at a step S7. The step S7 brings the handset 3 into a low power state. After a predetermined period in the low power state, the handset 3 wakes itself up at a step S8 in order to check that the delivery device 2 is functioning properly. The handset 3 therefore returns briefly to the active state (although the screen need not be switched on), in order to check the status of the delivery device 2 at a step S9. The step S9 requires the first radio transceiver 110 to be used to communicate with the delivery device 2. As soon as the status data from the delivery device 2 has been obtained and logged, the handset 3 returns to sleep at the step S10. This involves a return to the transition state, where the first radio (ANT) transceiver 110 of the handset 3 is switched off at a step S11, the second radio transceiver 120 (M2M link) is switched on at a step S12, the newly acquired status information is transmitted to the server 4 using the second radio transceiver 120 at a step S13, and then the handset fully powers off at a step S14, re-entering the low power state. It will be understood that the step S8 is shown to be initiated following a predetermined period of time in the low power state. However, another way in which the handset could wake up is in response to a user interaction with the handset 3, such as pressing a button, as represented at a step S15. However, in the case of the step S15, the handset 3 would fully wake up, returning to the step S1, rather than merely switching back on to perform a status check and switching back off again, as is the case with the step S8. It will be appreciated that, although the step S3 is shown to be initiated following a period of inactivity, it could instead be initiated by the user selecting a power down option on the user interface of the handset 3, or by depressing a button on the handset 3.

From the above, it will be understood that the portable medical device 2 may gather data relating to the condition of the patient. While the device is not being used for its intended purpose, it assumes a low power state in which it consumes very little or no power. The device may enter this state either in response to the user turning the device off (or into standby), or because the user has performed no actions on the handset 2 for a certain period. When the patient wishes to perform a task, they switch the device on, bringing it out of the suspended state, and complete the task. For some tasks (e.g. blood glucose reading) it may be unsafe for the wireless transmitter to be used during the task. At the point in time that the device returns to the suspended state, it is most likely that some data update has occurred as a result of the task, and that this provides a suitable cue to synchronise the data with the server. The device delays state change (via a transition state) while it connects to the remote database and performs synchronisation.

While embodiments of the present invention have been described with reference to an insulin delivery system, it will be appreciated that the present invention may be applied instead to the delivery of other drugs.

The invention claimed is:

1. A handset device, comprising:
   a first radio transceiver for receiving status information from a medical device worn by a patient, the first radio transceiver being operable only while the handset device is in an active state;
   a second radio transceiver for communicating the status information to a remote server, the second radio transceiver being inoperable when the handset device is in the active state; and
   a controller, responsive to a first predetermined condition to transition the handset device from the active state to a low power state in which both the first radio transceiver and the second radio transceiver are inoperable;
   wherein, during the transition from the active state to the low power state, the second radio transceiver is used to communicate the status information to the remote server.

2. The handset device according to claim 1, wherein the status information comprises information about the medical condition of the user.

3. The handset device according to claim 1, wherein the status information comprises information about the state of the medical device.

4. The handset device according to claim 1, wherein, during the transition from the active state to the low power state, a display screen of the handset device is switched off, and remains off while the handset device is in the low power state.

5. The handset device according to claim 1, wherein the first predetermined condition is a user input to the handset device.

6. The handset device according to claim 1, wherein the first predetermined condition is the non-use of the handset device for a predetermined period of time.

7. The handset device according to claim 1, wherein the first radio transceiver is one of a Bluetooth transceiver or an Advanced Network Technology (ANT) transceiver.

8. The handset device according to claim 1, wherein the second radio transceiver is one of a Wireless Fidelity (WiFi) transceiver, a mobile telecommunications network transceiver or a Global System for Mobile (GSM) radio transceiver.

9. The handset device according to claim 1, wherein the medical device is a therapeutic product delivery device, and the handset device controls the operation of the therapeutic product delivery device.

10. The handset device according to claim 9, wherein the first radio transceiver is used to carry control signals from the handset device to the therapeutic product delivery device to control the amount and/or timing of the delivery of a therapeutic product to the patient.

11. The handset device according to claim 1, wherein the medical device is a glucose meter.

12. The handset device according to claim 1, wherein the first radio transceiver is operable to receive status information from a plurality of medical devices.

13. The handset device according to claim 1, wherein the controller is responsive to a second predetermined condition to transition the handset device from the low power state to the active state.

14. The handset device according to claim 13, wherein the second predetermined condition is a user input to the handset.

15. The handset device according to claim 13, wherein the second predetermined condition is the handset having been in the low power state for a predetermined time period.

16. The handset device according to claim 15, wherein the controller is responsive to the handset having been in the low power state for a predetermined time period to transition the handset device from the low power state to the active state, obtain status information from the medical device via the first radio transceiver, and initiate a return transition from the active state to the low power state, wherein during the return transition from the active state to the low power state, the second radio transceiver is used to communicate the status information obtained from the medical device to the remote server.

17. A method of synchronising data between a handset device and a remote server, the handset having a first radio transceiver for receiving status information from a medical device worn by a patient, the first radio transceiver being operable only while the handset device is in an active state, and a second radio transceiver for communicating the status information to a remote server, the second radio transceiver being inoperable when the handset device is in the active state, the method comprising the steps of:
   responsive to a first predetermined condition, transitioning the handset device from the active state to a low power state in which both the first radio transceiver and the second radio transceiver are inactive; and
   during the transition from the active state to the low power state, communicating the status information to the remote server using the second radio transceiver.

18. A non-transitory computer-readable medium for storing a program capable of being executed on a processor of a handheld device, which when executed on a data processing device causes the data processing device to perform the steps of claim 17.

* * * * *